(12) United States Patent
Saari et al.

(10) Patent No.: US 10,180,379 B2
(45) Date of Patent: Jan. 15, 2019

(54) AIRFLOW DIVERTER FOR REDUCED SPECIMEN TEMPERATURE GRADIENT

(71) Applicant: MTS Systems Corporation, Eden Prairie, MN (US)

(72) Inventors: Byron John Saari, Minneapolis, MN (US); Paul Eric Meybaum, Maple Grove, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 14/733,513

(22) Filed: Jun. 8, 2015

(65) Prior Publication Data
US 2015/0355057 A1 Dec. 10, 2015

Related U.S. Application Data

(60) Provisional application No. 62/008,796, filed on Jun. 6, 2014.

(51) Int. Cl.
*G01N 1/04* (2006.01)
*G01N 3/18* (2006.01)

(52) U.S. Cl.
CPC .................. *G01N 1/04* (2013.01); *G01N 3/18* (2013.01); *G01N 2203/0222* (2013.01); *G01N 2203/0226* (2013.01)

(58) Field of Classification Search
CPC ............. Y10S 165/034; Y10S 165/161; Y10S 165/196; Y10S 165/214; Y10S 165/346;
(Continued)

(56) References Cited

U.S. PATENT DOCUMENTS

| 2,154,280 A | 4/1939 | Arpad |
| 2,579,424 A | 12/1951 | Gehman |

(Continued)

FOREIGN PATENT DOCUMENTS

| CN | 201166627 Y | 12/1993 |
| CN | 1412727 A | 4/2003 |

(Continued)

OTHER PUBLICATIONS

International Search Report and Written Opinion for corresponding International application No. PCT/US2015/034697 dated Sep. 1, 2015.

(Continued)

*Primary Examiner* — Hezron E Williams
*Assistant Examiner* — Tran M Tran
(74) *Attorney, Agent, or Firm* — Steven M. Koehler; Westman, Champlin & Koehler, P.A.

(57) ABSTRACT

An environmental chamber includes an enclosure having opposed walls each wall having an aperture of size to receive a test specimen support therethrough. The apertures are aligned with each other along on a reference axis. A forced air source is configured to supply forced air in a direction to intersect with the reference axis within the enclosure. A diverter is positioned between the forced air source and the reference axis. The diverter is configured to receive the forced air and control the air flow past different portions of the reference axis. The environmental chamber is used with a load frame having test specimen supports extending into the opposed apertures. A method of directing more force air at the test specimen supports than at at least a portion of the test specimen to maintain a selected temperature gradient in the test specimen is also provided.

17 Claims, 12 Drawing Sheets

(58) Field of Classification Search
CPC .............. Y10S 165/351; Y10S 165/352; B60H 1/00271; B60H 1/00507; F02M 35/116; F26B 21/028; F26B 21/022
See application file for complete search history.

(56) References Cited

U.S. PATENT DOCUMENTS

| | | | | |
|---|---|---|---|---|
| 2,904,993 | A | 9/1959 | Grover | |
| 3,224,259 | A | 12/1965 | De Nicola | |
| 3,492,862 | A | 2/1970 | Wallace | |
| 3,611,787 | A | 10/1971 | Annessa | |
| 3,795,134 | A | 3/1974 | Eichenbrenner | |
| 4,093,021 | A * | 6/1978 | Groom .................. | B64D 13/00 165/126 |
| 4,191,402 | A | 3/1980 | Michlin | |
| 4,399,485 | A * | 8/1983 | Wright ............... | H05K 7/20009 165/80.3 |
| 4,537,080 | A | 8/1985 | Christiansen | |
| 4,549,072 | A | 10/1985 | Brist | |
| 4,628,992 | A * | 12/1986 | Kennedy ............ | H05K 7/20145 165/123 |
| 4,711,587 | A | 12/1987 | Cocito | |
| 4,721,000 | A | 1/1988 | Scanlon | |
| 4,730,233 | A * | 3/1988 | Osterman .......... | H05K 7/20572 361/693 |
| 4,772,299 | A * | 9/1988 | Bogusz .................. | B01D 45/04 188/264 AA |
| 4,909,085 | A | 3/1990 | Hardy | |
| 4,929,541 | A * | 5/1990 | Potter .................... | F23D 14/34 431/351 |
| 4,990,312 | A * | 2/1991 | Rucker .................. | G01N 25/50 374/8 |
| 5,054,324 | A | 10/1991 | Pohl | |
| 5,095,757 | A * | 3/1992 | Larsen .................... | G01N 3/04 73/857 |
| 5,119,681 | A | 6/1992 | Miszczak | |
| 5,237,876 | A | 8/1993 | Liu | |
| 5,269,181 | A | 12/1993 | Gibson | |
| 5,286,108 | A | 2/1994 | Whatley et al. | |
| 5,302,023 | A * | 4/1994 | Larsen .................... | G01N 3/18 374/46 |
| 5,329,820 | A | 7/1994 | McMahon | |
| 5,481,923 | A | 1/1996 | Ohmi | |
| 5,505,095 | A | 4/1996 | Raymond | |
| 5,581,040 | A | 12/1996 | Lin | |
| 5,945,607 | A * | 8/1999 | Peppel .................... | G01N 3/04 73/831 |
| 6,000,464 | A * | 12/1999 | Scafidi ............... | H05K 7/20572 165/104.33 |
| 6,018,458 | A * | 1/2000 | Delia .................. | H05K 7/20154 165/80.3 |
| 6,252,161 | B1 * | 6/2001 | Hailey .................. | H05K 9/0041 174/383 |
| 6,272,012 | B1 * | 8/2001 | Medin ...................... | G06F 1/20 165/104.26 |
| 6,280,319 | B1 * | 8/2001 | Wong .................. | H05K 7/20581 415/211.2 |
| 6,526,837 | B1 | 3/2003 | Grote et al. | |
| 6,625,018 | B1 * | 9/2003 | Augustin ................ | G06F 1/182 165/80.3 |
| 6,629,466 | B2 | 10/2003 | Grote ........................ | G01N 3/04 73/857 |
| 6,776,400 | B1 * | 8/2004 | Laneuville ............. | F02M 25/08 123/184.25 |
| 6,974,178 | B2 * | 12/2005 | Ortega .................. | B62D 35/001 296/180.1 |
| 7,278,389 | B2 * | 10/2007 | Kirakosyan ...... | F02M 35/10019 123/184.53 |
| 7,568,397 | B2 | 8/2009 | Merendino | |
| 7,739,919 | B2 | 6/2010 | Sikkila | |
| 8,634,190 | B2 * | 1/2014 | Nguyen ............... | H05K 7/1445 361/679.5 |
| 9,696,218 | B2 | 7/2017 | Lemmer | |
| 2014/0116773 | A1 * | 5/2014 | Yang .................. | H05K 7/20727 174/650 |

FOREIGN PATENT DOCUMENTS

| | | |
|---|---|---|
| CN | 1987408 A | 6/2007 |
| CN | 101305273 | 11/2008 |
| CN | 101526451 A | 9/2009 |
| CN | 101614640 A | 12/2009 |
| CN | 201732028 U | 2/2011 |
| DE | 1920767 A1 | 11/1970 |
| DE | 4101321 A1 | 7/1992 |
| EP | 0573952 A2 | 12/1993 |
| FR | 2378273 A1 | 8/1978 |
| GB | 1547552 A | 6/1979 |
| JP | 5999331 B2 | 6/1984 |
| JP | 60154138 A | 8/1985 |
| JP | 60178334 A | 9/1985 |
| JP | H102847 A | 1/1998 |
| JP | 2009-294136 A | 12/2009 |
| SU | 361418 A1 | 12/1972 |
| SU | 538274 A1 | 12/1976 |
| SU | 9388088 A1 | 6/1982 |
| WO | 9857142 A1 | 12/1998 |

OTHER PUBLICATIONS

MTS Specification Sheet No. 651.04, Series 651 Environmental Chambers.
MTS Application Notes, Model 657.03 High Temperature Furnace.
Response as filed for U.S. Appl. No. 13/840,760 dated Jan. 30, 2017.
Advisory Action for U.S. Appl. No. 13/840,760 dated Feb. 14, 2017.
Response as filed for U.S. Appl. No. 13/840,760 dated Aug. 22, 2016.
Final Office Action for U.S. Appl. No. 13/840,760 dated Nov. 30, 2016.
Office Action for U.S. Appl. No. 13/840,760 dated May 21, 2015.
Response as filed for U.S. Appl. No. 13/840,760 dated Oct. 20, 2015.
Final Office Action for U.S. Appl. No. 13/840,760 dated Jan. 7, 2016.
Response as filed for U.S. Appl. No. 13/840,760 dated Apr. 7, 2016.
Advisory Action for U.S. Appl. No. 13/840,760 dated May 4, 2016.
Office Action for U.S. Appl. No. 13/840,760 dated May 20, 2016.
Chinese Office Action from the State Intellectual Property Office of People's Republic of China for Chinese patent application No. 201380052316.9, dated Apr. 13, 2017.
International Search Report and Written Opinion for corresponding International patent application No. PCT/US2013/053696, filed Aug. 6, 2013, dated Apr. 3, 2014. .
Communication relating to the results of the Partial International Search for corresponding PCT/US2013/053696 filed Aug. 6, 2013.
Chinese Office Action from the State Intellectual Property Office of People's Republic of China for Chinese patent application No. 201380052316.9, dated Mar. 2, 2016.
MTS Systems Corporation, Grip Set Assy-680.018-OX, at least as early as Aug. 7, 2012.
Notice of Reasons for Rejection for Japanese Patent Application No. 2016-571003, dated Oct. 29, 2018, with English translation.

* cited by examiner

AIRFLOW DIVERTER FOR REDUCED SPECIMEN TEMPERATURE GRADIENT

CROSS-REFERENCE TO RELATED APPLICATION

This application claims the benefit of U.S. Provisional Application Ser. No. 62/008,796, filed Jun. 6, 2014, having the same title, and is hereby incorporated by reference in its entirety.

BACKGROUND

The discussion below is merely provided for general background information and is not intended to be used as an aid in determining the scope of the claimed subject matter.

Common tests performed on polymer and metallic materials involve a cyclic or monotonic applied stress. These tests often apply tensile forces and/or compressive forces to a specimen. Specimens may include, by way of example only and not by way of limitation, tensile and compressive specimens in dog bone and cylindrical shapes, etc. Gripping mechanisms for holding specimens may include, by way of example only and not by way of limitation, tensile grips, compression platens, wedge action grips, shear grips such as double lap shear grips, tearing energy grips, bend fixtures, etc. Tests are often performed in a load frame with an environmental chamber used to expose the specimen under test to a particular thermal environment. The temperature is often controlled and usually varied throughout the test. The mechanical properties of the material are evaluated by imposing an excitation motion (or force) on the specimen and measuring the resultant force (or motion) response of the specimen.

From the relationship of the response output to the excitation input, characteristics of the specimen material can be deduced. Most theoretical models for the polymers predict a response which is dependent on frequency, temperature, and amplitude. Most empirical testing maps the response as a function of varied frequency, temperature, and amplitude. One such example is the measure of the dynamic moduli of polymer materials, for instance, the storage modulus and loss modulus for dynamic mechanical analysis (DMA). In the particular case of polymer testing, since the mechanical properties (dynamic moduli) are very temperature dependent, it is important that the specimen under test be of a homogenous and stable temperature during the mechanical measurement. This thermal environment is key in obtaining repeatable and consistent empirical data.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the disclosure includes an environmental chamber having an enclosure with opposed walls each wall having an aperture of size to receive a test specimen support therethrough. The apertures are aligned with each other along on a reference axis. A forced air source is configured to supply forced air in a direction to intersect with the reference axis within the enclosure. A diverter is positioned between the forced air source and the reference axis. The diverter is configured to receive the forced air and control the air flow past different portions of the reference axis. The environmental chamber is used with a load frame having test specimen supports extending into the opposed apertures.

Another aspect of the disclosure is a load frame having a support structure, an actuator connected to the support structure and a pair of test specimen supports connected to the support structure and the actuator and configured to hold a test specimen therebetween and on a reference axis, each test specimen support including a test specimen support configured to hold a portion of the test specimen. The load frame includes the environmental chamber as described above where each aperture is of size to receive one of the test specimen supports therethrough.

The environmental chamber, load frame and method above can include one or more of the following features.

The diverter can be configured to reduce air flow at an inner portion of the reference axis remote from each of the apertures and increase air flow at remote portions of the reference axis, each remote portion being located between the inner portion and one of the apertures. The diverter can include surfaces to deflect air flow toward each of the remote portions of the reference axis, where each of the surfaces can be oriented oblique to the air flow.

The diverter can include a first of one or more apertures therethrough to direct air flow to each of the remote portions of the reference axis, and if desired, a second of one or more apertures therethrough configured to direct air flow to the inner portion of the reference axis. In one embodiment, the second of one or more apertures is disposed between a pair of said first of one or more apertures. Each of the first of one or more apertures and/or the second of one or more apertures can be disposed one or more flat members, where the flat member(s) are oriented oblique to the reference axis or parallel to the reference axis.

In further embodiment, the diverter includes a mount configured to adjustably fix the diverter at a selected distance from the reference axis. The diverter can be mounted in the enclosure in a spaced apart relation to a third aperture or inlet (i.e. outlet for the forced air support) that provides forced air into the enclosure. In yet a different embodiment, the diverter is mounted so as to cover at least a part of the third aperture, where the third aperture can be disposed on a conduit adjustable in length and configured to convey the forced air.

Yet another aspect is a method of maintaining a selected temperature gradient of a test specimen during application of loads or displacements with a load frame having a support structure and an actuator, comprising: supporting the test specimen in an environmental chamber with a pair of test specimen supports operably connected to the actuator and the support structure so as to hold the test specimen on a reference axis, each test specimen support having a portion extending into the environmental chamber through a corresponding aperture; and supplying forced air into the chamber; and directing more air at each of the portions of the test specimen supports than at at least a portion of the test specimen to control a temperature gradient across the test specimen during testing.

In one embodiment, directing more air at each of the portions of the test specimen supports than at at least a portion of the test specimen comprises using a diverter to control air flow. The method can also include adjusting a position of the diverter in the environmental chamber and/or including one or more of the features described above.

DETAILED DESCRIPTION

Figure 1:
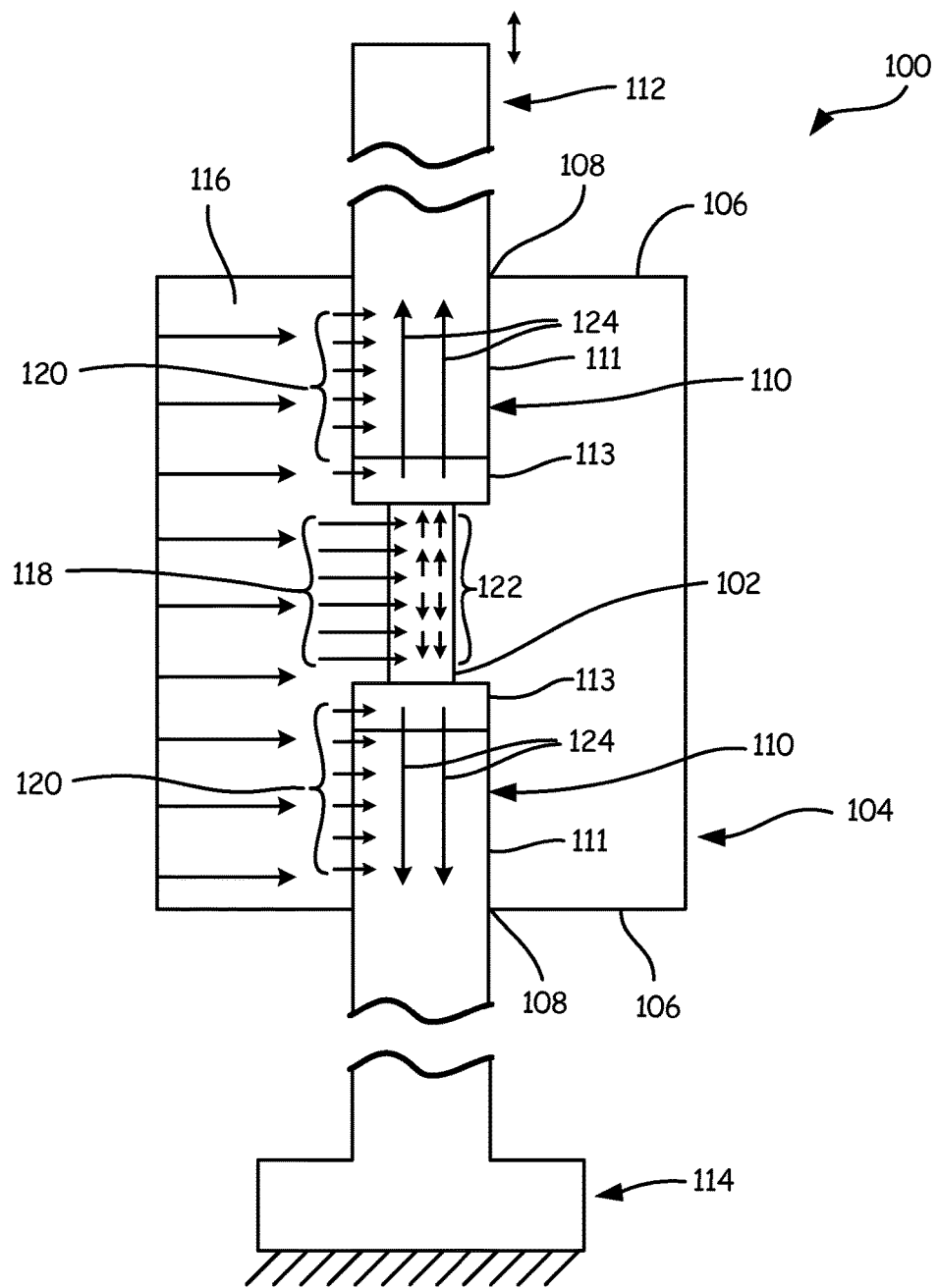
FIG. 1 is a block diagram of a load frame with heated air flow.
Figure 10:
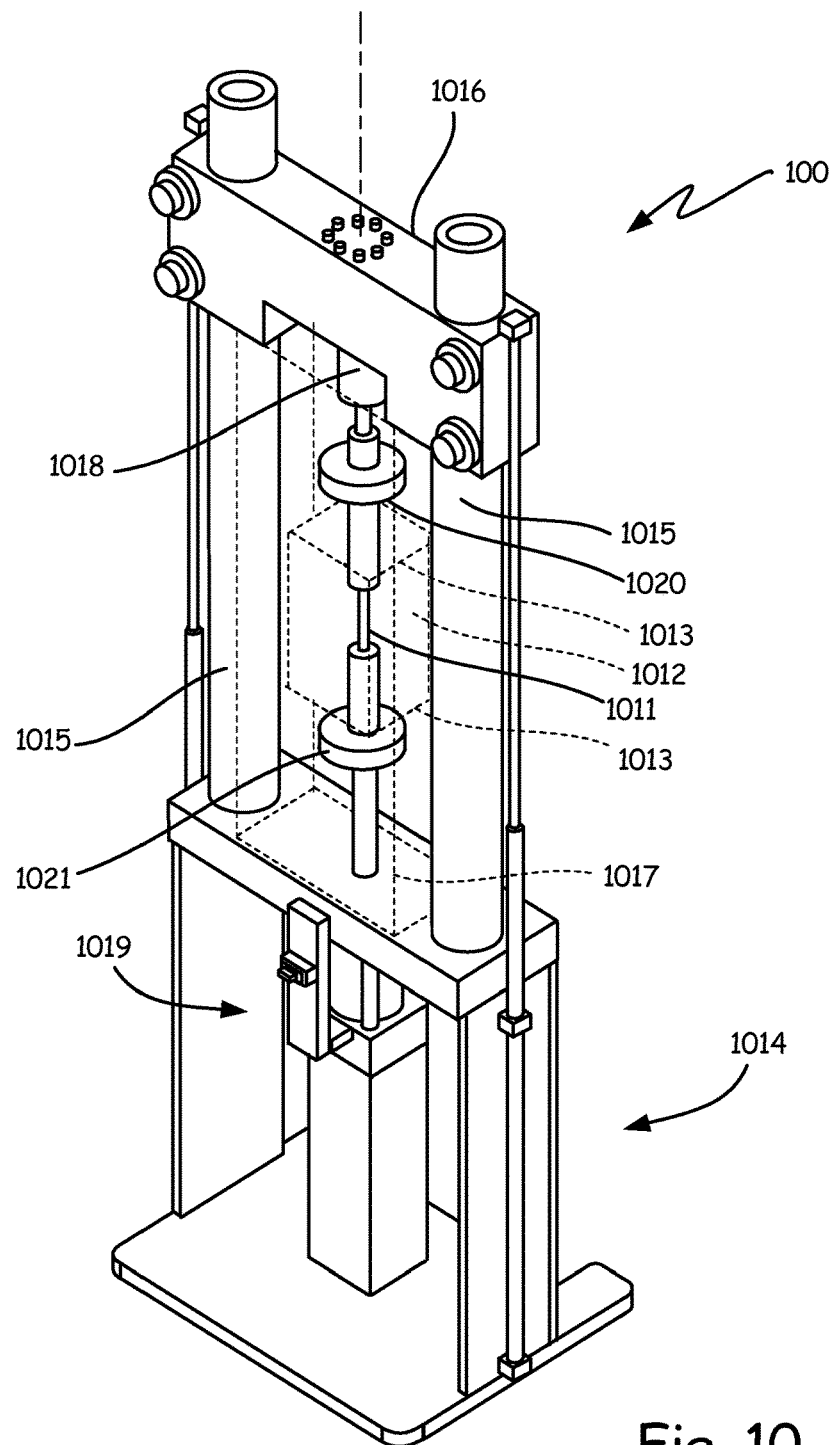
FIG. 10 is a perspective view of a load frame with an environmental chamber.

A load frame indicated schematically at 100 in FIG. 1 is shown in greater detail in FIG. 10. Load frame 100 is generally used for loading a test specimen shown schematically at 102. The specimen 102 is located in the interior of an environmental chamber 104 forming an enclosure with a pair of end walls 106 having openings 108 through which extension support assemblies 110 extend. The chamber 104 is supported relative to the load frame 100 in any desired manner, the details of which are not pertinent to the present disclosure. Extension assemblies 110 support the specimen 102 in a load path between an excitation motion input 112 and a force transducer 114, and each includes a test specimen support 111 typically connected to a gripping mechanism 113, shown schematically, such as those described above. Such excitation motion inputs, force transducers, and the relative positions thereof in the test system 100 may vary depending on the specific test system employed. Nevertheless, these aspects are well known, and the details of which are not pertinent to the present disclosure.

Referring to FIG. 10, a load frame indicated generally at 100 is shown schematically and is used for loading a test specimen shown schematically at 1011. The specimen 1011 is located in the interior of an environmental chamber 1012 forming an enclosure with a pair of opposed end walls 1013. The chamber 1012 can be disposed within another enclosure 1017. The chamber 1012 is supported relative to the load frame 100 in any desired manner, the details of which are not pertinent to the present invention disclosure. As illustrated, the load frame 100 has a support structure having base 1014, a pair of upright columns 1015 and a cross head 1016. The cross head 1016 supports a test specimen support 1020 having aspects of the present disclosure. A similar, if not identical, test specimen support 1021 is illustrated at a lower end of the environmental chamber 1012. In the embodiment illustrated, the test specimen support 1021 is coupled to an actuator (indicated schematically at 1019) that is located in the base 1014. Such actuators are well known, the details of which are not pertinent to the present disclosure. Generally, the actuator 1019 and the support structure are configured so as to apply loads or displacements to the test specimen 1011 using the test specimen supports 1020, 1021. A load cell 1018 is often provided to measure applied loads.

At this point, it should be noted aspects of the present disclosure are not limited to the load frame 100 of the exemplary embodiment, nor are aspects of the present disclosure limited to only applying loads to the test specimen 1011, although aspects of the present disclosure are particularly advantageous when loads are applied since such loads are applied through the test specimen supports 1020 and 1021.

Environmental chambers are commonly used to subject the test specimen 1011 to high or low temperature environments in order to obtain measurements indicative of properties of the test specimen 1011. Since at least portions of the test specimen supports 1020 and 1021 are also subjected to the same or similar environment as the test specimen, the test specimen supports 1020 and 1021 (e.g., extension assemblies such as assemblies 110 schematically illustrated) must perform satisfactorily when subjected to the high or low temperature environment. In the case of load frames such as load frame 100, the test specimen supports 1020, 1021 transmit or impart loads to the test specimen 1011, and therefore, they must impart these loads when the holders 1020, 1021 are also operating in the high or low temperature environment.

Extension assemblies 110 or supports 111 are part of test specimen grips well known in the material testing field. The mechanisms used to hold the ends of the test specimen may take any number of well-known forms including but not limited to displaceable wedges and clamping collets. Other forms of test specimen supports are illustrated in U.S. Pat. Nos. 5,095,757 and 5,945,607 and which is hereby incorporated by reference in its entirety. These and other forms of test specimen receivers can be used with aspects of the present invention herein described and/or illustrated.

Environmental chambers are commonly used to subject the test specimen 102 to high or low temperature environments in order to obtain measurements indicative of properties of the test specimen 102. As at least portions of the extension assemblies 110 are also subjected to the same or similar environment as the test specimen 102, the thermal properties of the extension assemblies 110 are also a factor in obtaining measurements.

In order to change the temperature of a specimen such as specimen 102, thermal chambers such as chamber 104 typically used forced air flow of heated or cooled air within the chamber 104 directed across the specimen 102 and the specimen attachment region. Since the temperature range for a typical polymer test is in the −150 to 350° C. range (but not limited to this range), and as many different temperatures may be used during a test, fast temperature changes may be desired. Forced air convection is typically used over natural air convection, and a forced convection environmental chamber is the most applicable heating/cooling device to control specimen temperature quickly.

The extension assemblies 110 are part of the load path defining a reference axis 107, including at least a portion of the extension assemblies 110, e.g. test specimen support 111, being inside the environmental chamber 104, and as such, high stiffness and low mass for the extension assemblies 110 is desired. A high stiffness, low mass design constraint often leads to material and geometry selections for extension assemblies 110 which have a high thermal conductive rate, and relatively lower thermal convective rate, particularly with respect to the specimen 102 under test. The extension assemblies 110 become a conductive heat transfer path from the interior of the environmental chamber 104 to components outside the environmental chamber 104, which is most often at some temperature unequal to the desired specimen temperature and the environmental chamber air temperature. In contrast, the specimens are often polymer materials having a high thermal convective rate, and a relatively lower thermal conductive rate relative to the extension assemblies 110. Further, the specimen diameter is also usually smaller than the diameter of the extension assemblies 110, which results in a higher convective heat transfer for the specimen section.

Extension assemblies 110 that extend into an environmental chamber are subjected to the same environmental conditions as the specimen 102 to be tested. Traditional methods by which the temperature of extension assemblies are controlled include fluid cooling or fluid heating, such as by running cooled or heated water or air through the extension assemblies. Heat draw from/to fluid cooling/heating can lead to very large temperature gradients. Further, fluid cooling or heating extension assemblies inside of an environmental chamber can be very difficult to implement. In an advantageous embodiment, extension assemblies 110 described herein are not cooled or heated, except by convective air flow in the chamber, and internal conductive heat flow. In other words, the extension assemblies 110 or supports 111 extending into the environmental chamber do not include any supplemental heating or cooling systems or features, thereby providing significant cost savings because a much simpler support can be used.

In the case of a high temperature environment in the environmental chamber 104, the air temperature is always higher than the specimen temperature. Therefore, all convective heat transfer from the air flow is into the specimen 102 and into the extension assemblies 110 as shown in FIG. 1, with arrows of longer length indicating a higher heat transfer rate. Specifically, horizontal arrows indicate convective transfer, and vertical arrows represent conductive heat transfer. Forced hot air indicated by arrows 116 results in convective heat transfer into the specimen 102 as indicated by arrows 118, and convective heat transfer into the extension assemblies 110 as indicated by arrows 120. Conductive heat transfer in specimen 102 is indicated by arrows 122, and conductive heat transfer in extension assemblies 110 is indicated by arrows 124. All conductive heat transfer leads out of the chamber 104 through the extension assemblies 110. The thermal flow for this embodiment is from the forced hot air, to the specimen 102 and extension assemblies 110, and out of the specimen 102 to the extension assemblies, and then out of the chamber 104.

Figure 2:
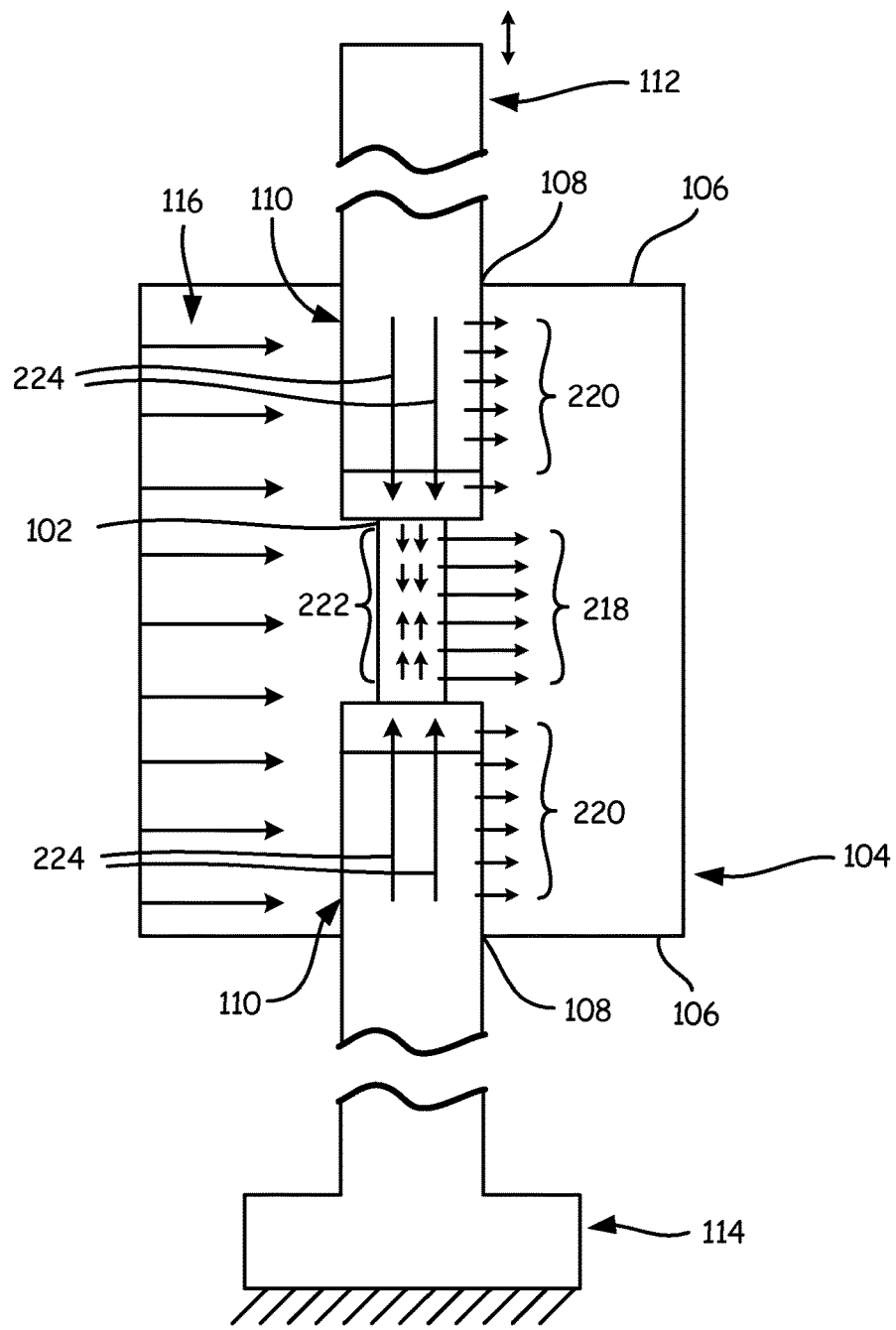
FIG. 2 is a block diagram of a load frame with cooled air flow.

In the case of a cold temperature environment in the environmental chamber 104, the air temperature is always lower than the specimen temperature. Therefore, all convective heat transfer from the air flow is out of the specimen and out of the extension assemblies as shown in FIG. 2, with arrows of longer length indicating a higher heat transfer rate. Specifically, horizontal arrows indicate convective transfer, and vertical arrows represent conductive heat transfer. Forced cold air indicated by arrows 116 results in convective heat transfer from the specimen 102 as indicated by arrows 218, and convective heat transfer from the extension assemblies as indicated by arrows 220. Conductive heat transfer in specimen 102 is indicated by arrows 222, and conductive heat transfer in extension assemblies 110 is indicated by arrows 224. All conductive heat transfer leads into the chamber 104 through the extension assemblies 110. The thermal flow for this embodiment is from the exterior of the chamber 104, into the extension assemblies 110, into the specimen 102 from the extension assemblies 110, and out of the specimen 102 and extension assemblies 110 to the chamber 104.

Because of the typically different thermal qualities of the extension assemblies 110 and the specimen 102, and the conductive heat transfer into or out of the specimen 102 from the contact with the extension assemblies 110, there can be difficulty in obtaining a uniform temperature gradient within a specimen in the presence of a convective airflow field. Due to the relatively low thermal conductivity combined with the high convective heat transfer in the specimen 102, the center section of the specimen 102 can form a hot spot in a heated environment (FIG. 1). The high thermal conductivity of the extension assemblies 110 keep the assemblies 110 relatively cool (at least with respect to the specimen 102) in a heated environment, and create a heat sink for thermal energy flowing from the specimen 102 into the assemblies 110. The relatively low convective heat transfer coefficient of the typically metallic assemblies 110 can make the thermal gradient problem in the specimen 102 even worse since the lack of convective heating from the air to the extension assemblies 110 also keeps the assemblies 110 cooler with respect to the specimen 102. Similar difficulty is found in obtaining uniform temperature gradient within a specimen in the presence of a cooled environment (FIG. 2).

In one embodiment, a diverter is positioned in the forced air flow path, to divert at least some of the heated or cooled air from the center region (coinciding with an inner portion of the reference axis 107) of the specimen 102 to the extension assemblies 110 (each located at a remote portion of the reference axis 107 remote from the inner portion of the reference axis 107). The various embodiments of the diverter reduce the convective heat transfer coefficient in the specimen region, which, for example, reduces the hot spot in the center of the specimen 102. This reduced hot spot allows a less drastic temperature gradient across the specimen vertical section.

Figure 3:
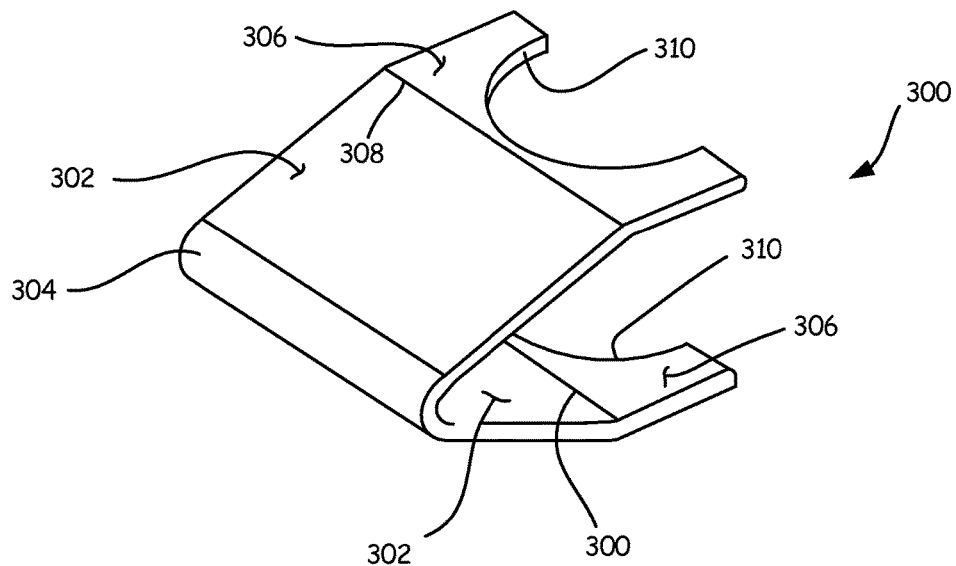
FIG. 3 is a perspective view of a diverter according to an embodiment of the present disclosure.
Figure 4:
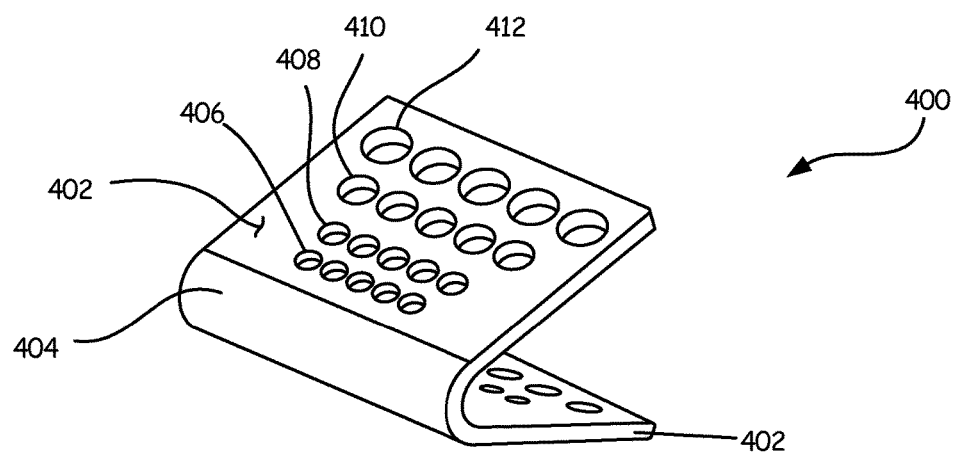
FIG. 4 is a perspective view of a diverter according to another embodiment of the present disclosure.

Example embodiments of diverters 300 and 400 are shown, respectively, in FIGS. 3 and 4. Diverter 300 is seen in perspective in FIG. 3. Diverter 300 has a wedge shape having wedge walls or surfaces 302 extending from a wedge apex 304 in a diverging manner. Diverter 300 may have legs 306 extending substantially parallel to one another from ends 308 of wedge walls 302 remote from apex 304. Legs 306 in one embodiment have a semi-circular cutout 310 to reduce or prevent air flow toward a specimen. The shape of the cutout 310 can be similar to the shape of the outer surfaces of the specimen 102, if desired. The diverter 300 is shown positioned in an air flow path in FIG. 5 where the surfaces 302 are oriented oblique to the air flow or the reference axis 107.

Figure 5:
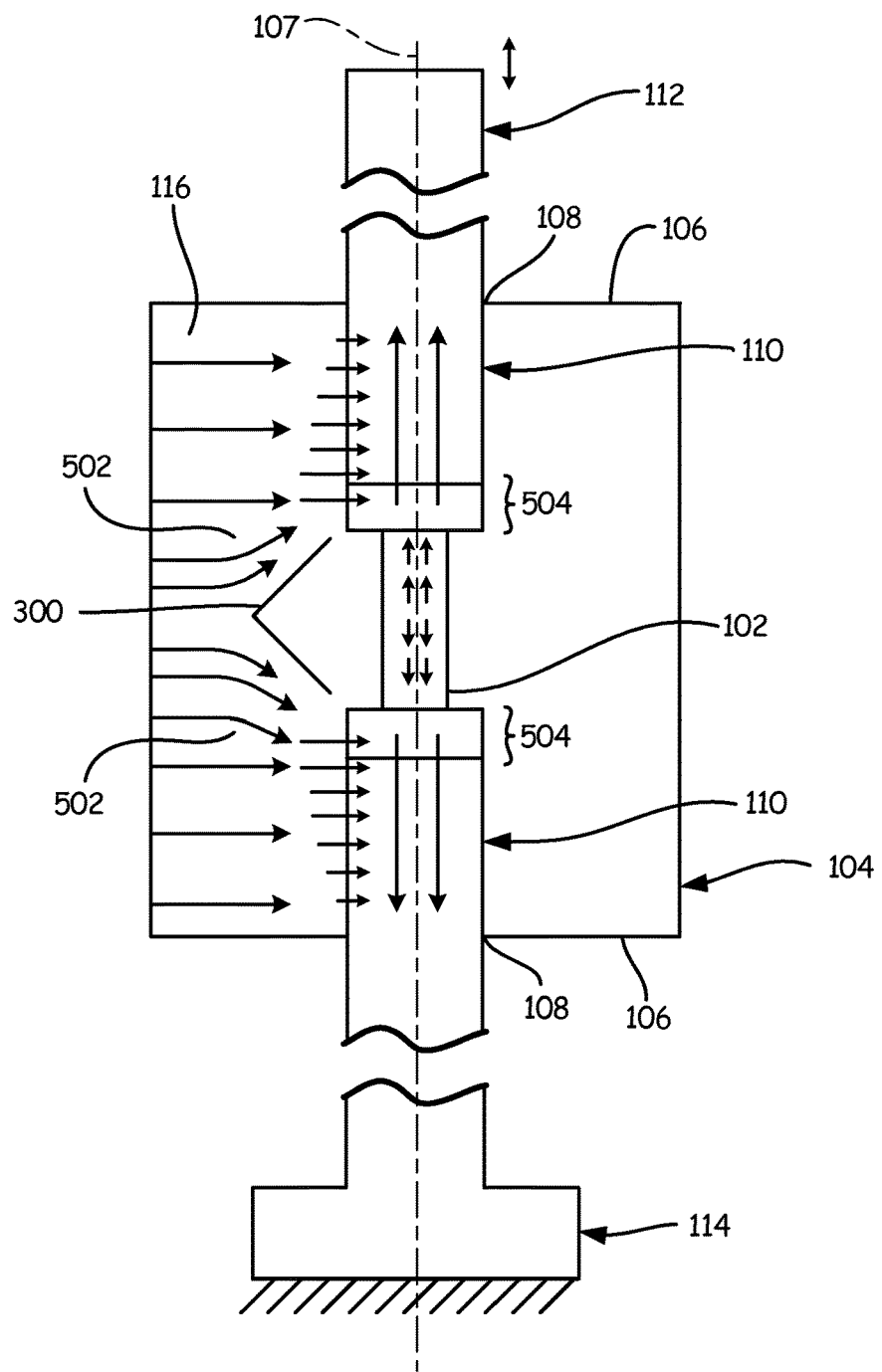
FIG. 5 is a block diagram of a diverter enabled embodiment of the present disclosure.

Referring also to FIG. 5, diverter 300 placed in the flow path of air flow 116 reduces the heat transfer in the specimen region, particularly the center thereof, by reducing the amount of local air flow at the specimen 102. Since the convective heat transfer coefficient is proportional to the quantity of air flow, lower quantity of air flow results in a lower heat transfer coefficient. The forced air flow 116 is diverted at 502 away from the center of the specimen 102, and toward the extension assemblies 110. This substantially reduces the amount of convective heating of the specimen 102, and increases the amount of convective heating of the extension assemblies 110, especially in the area 504 of the extension assemblies 110 that are closest to the specimen 102. This additional airflow compensates for the relatively higher thermal conductivity of the assemblies 110 relative to the specimen 102 so as to increase the temperature of the extension assemblies 110, when compared with the testing environment without the diverter 300, and makes and/or maintains the extension assemblies 110 closer in temperature to that of the specimen 102, reducing conductive heat flow from the specimen 102 to the extension assemblies 110 by reducing the temperature gradient between the specimen 102 and the extension assemblies 110, and then as a result, reducing the temperature gradient within the specimen.

Diverter 400 is seen in perspective in FIG. 4. Diverter 400 has a wedge shape similar to that of diverter 300, having diverging wedge walls 402 extending from a wedge apex 404. Diverter 400 has in one embodiment a plurality of openings in each of its walls 402. The openings are smallest at 406 closest to the wedge apex 404, and increase (e.g. gradually) to larger openings 408, 410, and 412 the farther the openings are from the wedge apex 404. While four rows of openings are shown, it should be understood that a greater or fewer number of rows of openings (or other patterns of the openings) may be used without departing from the scope of the disclosure. Further, the openings in another embodiment may have multiple rows of openings of the same size without departing from the scope of the disclosure. The diverter 400 is shown positioned in an air flow path in FIG. 6.

Figure 6:
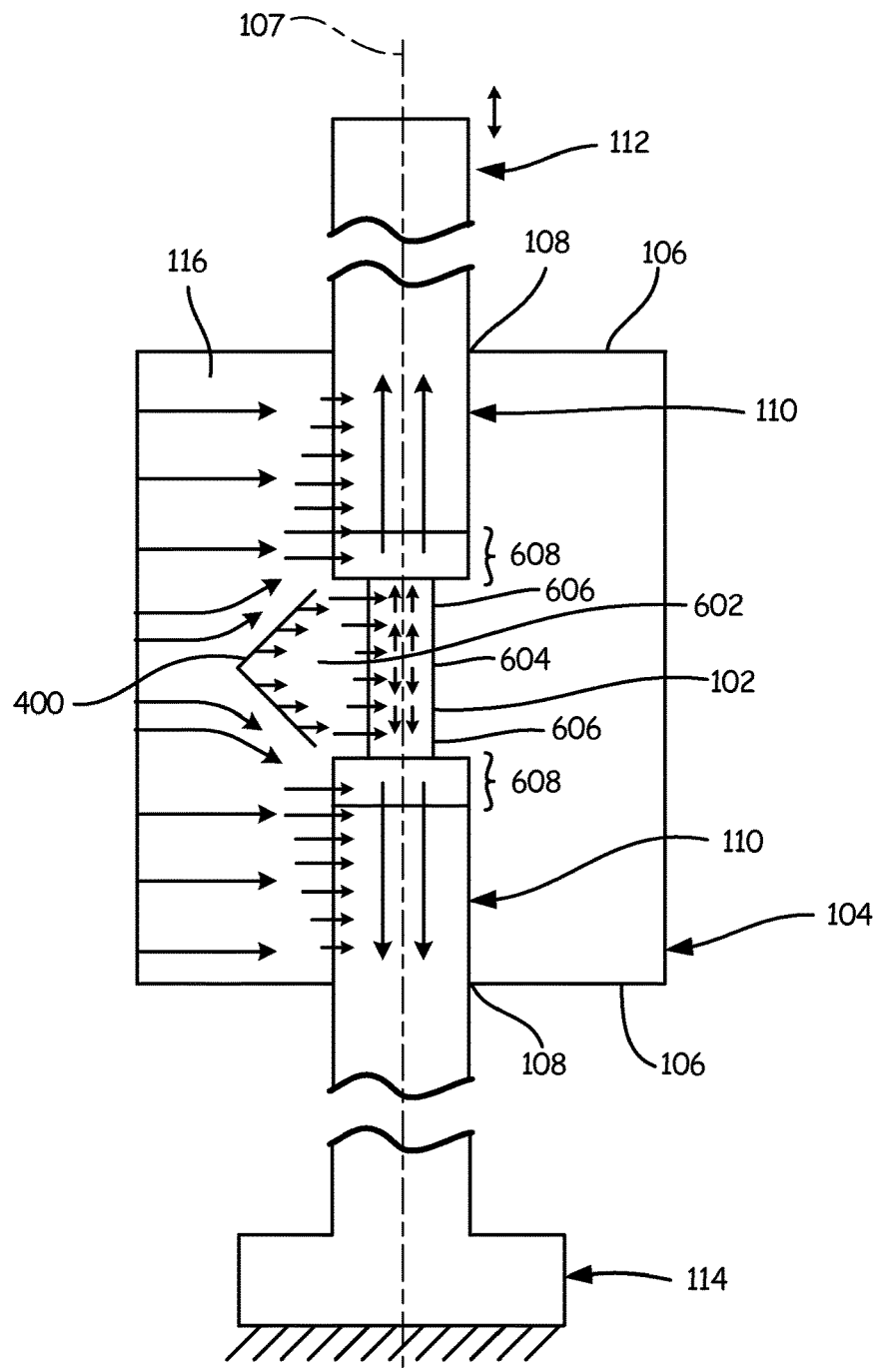
FIG. 6 is a block diagram of another diverter enabled embodiment of the present disclosure.

Referring also to FIG. 6, diverter 400 placed in the flow path of air flow 116 reduces the heat transfer in the specimen region by reducing the local air flow velocity at the specimen 102 in a manner similar to that described above with respect to diverter 300. Since the convective heat transfer coefficient is proportional to the air velocity, lower air velocity results in a lower heat transfer coefficient. The forced air flow 116 is diverted at 502 away from the center of the specimen 102, and toward the extension assemblies 110. Further down the legs 402 from the wedge apex 404, the openings 406, 408, 410, and 412 allow an increasing amount of air flow from forced air flow 116 through to the specimen 102, as indicated at 602, with convective heating greater near ends of the specimen 102 closest to the extension assemblies 110, indicated at 606. This additional airflow compensates for the relatively higher thermal conductivity of the assemblies 110 relative to the specimen 102 so as to reduce the amount of convective heating of the specimen at the center 604 of specimen 102, and increases the amount of convective heating of the extension assemblies 110, especially in the area 608 of the extension assemblies 110 that are closest to the specimen 102 when compared with the testing environment without the diverter 400. This partial diversion of air flow increases the temperature of the extension assemblies, and makes and/or maintains the extension assemblies 110 closer in temperature to that of the specimen 102, reducing conductive heat flow from the specimen 102 to the extension assemblies 110 by reducing the temperature gradient between the specimen 102 and the extension assemblies 110, and then as a result, reducing the temperature gradient within the specimen.

Diverters such as diverters 300 and 400 are in one embodiment positioned in close proximity to the specimen 102, so as to divert as much of air flow 116 away from the specimen as desired, with at least a majority of air flow 116 directed at the specimen 102 being diverted away from specimen 102 by diverter 300, and less air flow 116 diverted away from specimen 102 by diverter 400 in comparison to the air flow diverted by diverter 300, with each diverter 300 and 400 reducing the temperature gradient between specimen 102 and extension assemblies 110, and then as a result, reducing the temperature gradient within the specimen. Diverters 300 and 400 may be mounted within chamber 104 in a number of ways without departing from the scope of the disclosure. For example only and not by way of limitation, diverters could be mounted for example with support plates and/or support assemblies to an inside portion of the environmental chamber 106, such as to a wall or a door thereof, or diverters 300 and 400 could be mounted to one or both of the extension assemblies 110 disposed in the environmental chamber 106, or the like.

Diverters such as diverters 300 and 400 are positioned as shown in close proximity to the specimen 102. It should be understood that the exact positioning of the diverters 300 and 400 may be closer to or farther from the specimen 102 without departing from the scope of the disclosure. Further, multiple diverter designs are possible that divert air flow from the specimen 102, or that divert more air flow toward portions of the extension assemblies 110 as opposed to the specimen 102, and are within the scope of the disclosure.

Figure 7:
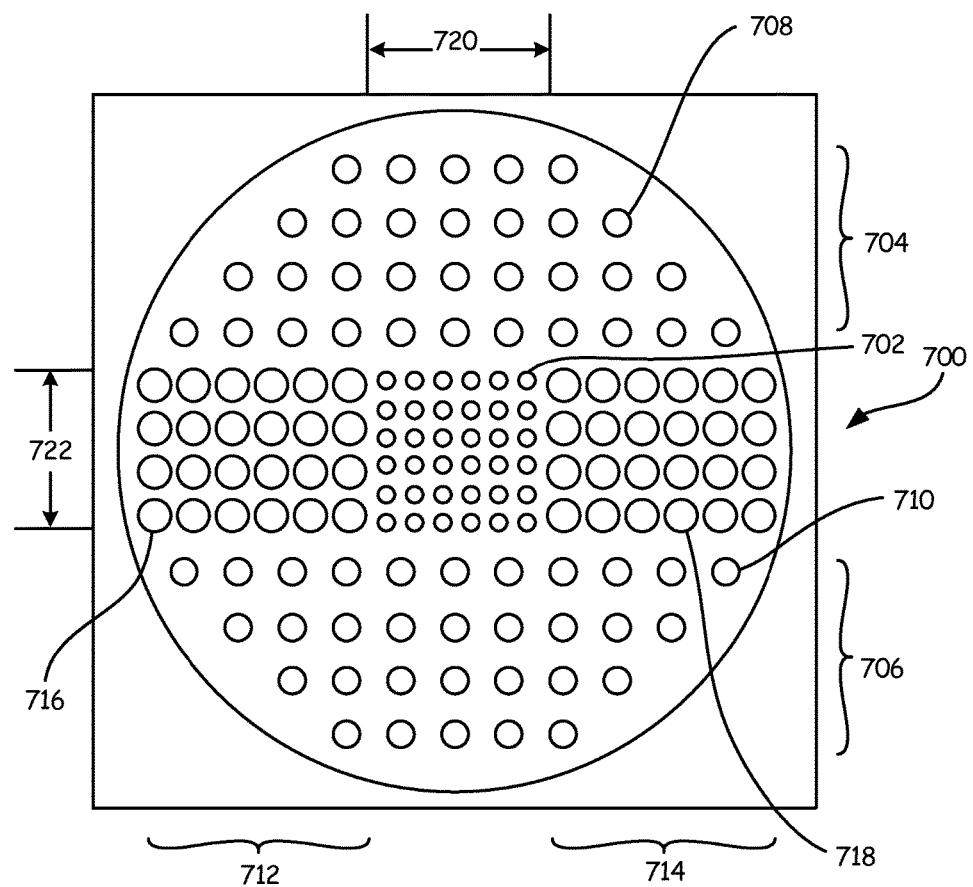
FIG. 7 is an elevation view of a diverter according to an embodiment of the present disclosure.

FIG. 7 shows a diverter 700 that may be used in another embodiment to reduce the temperature gradient within a specimen 102 assemblies. A smaller temperature gradient between a specimen such as specimen 102 and extension assemblies such as assemblies 110 may help to reduce the temperature gradient within the specimen. Diverter 700 in the exemplary embodiment may be considered a baffle since the diverter 700 covers or is otherwise disposed in a channel or passageway or at an end thereof through which air flow 116 is introduced onto the specimen. In this embodiment, the air flow conduit opening is circular, and the diverter 700 is therefore circular. It should be understood that different air flow conduit opening shapes may be accommodated with diverters of a shape matching the conduit opening without departing from the scope of the disclosure.

Diverter 700 has a plurality of openings of different sizes therein. At a center of the diverter, openings 702 are small. At top and bottom portions 704 and 706 of the diverter 700, openings 708 and 710 are larger than openings 702. At sides 712 and 714 of the diverter 700, openings 716 and 718 are larger than openings 702, 708, and 710. As air flow passes through the diverter 700, more air moves through openings 716 and 718 than through openings 708 and 710, and more air moves through openings 708 and 710 than through openings 702. In one embodiment, the width 720 and height 722 of the section of the diverter 700 containing openings 702 is approximately sized to a height and width of the specimen 102, although that need not be the case.

Figure 8:
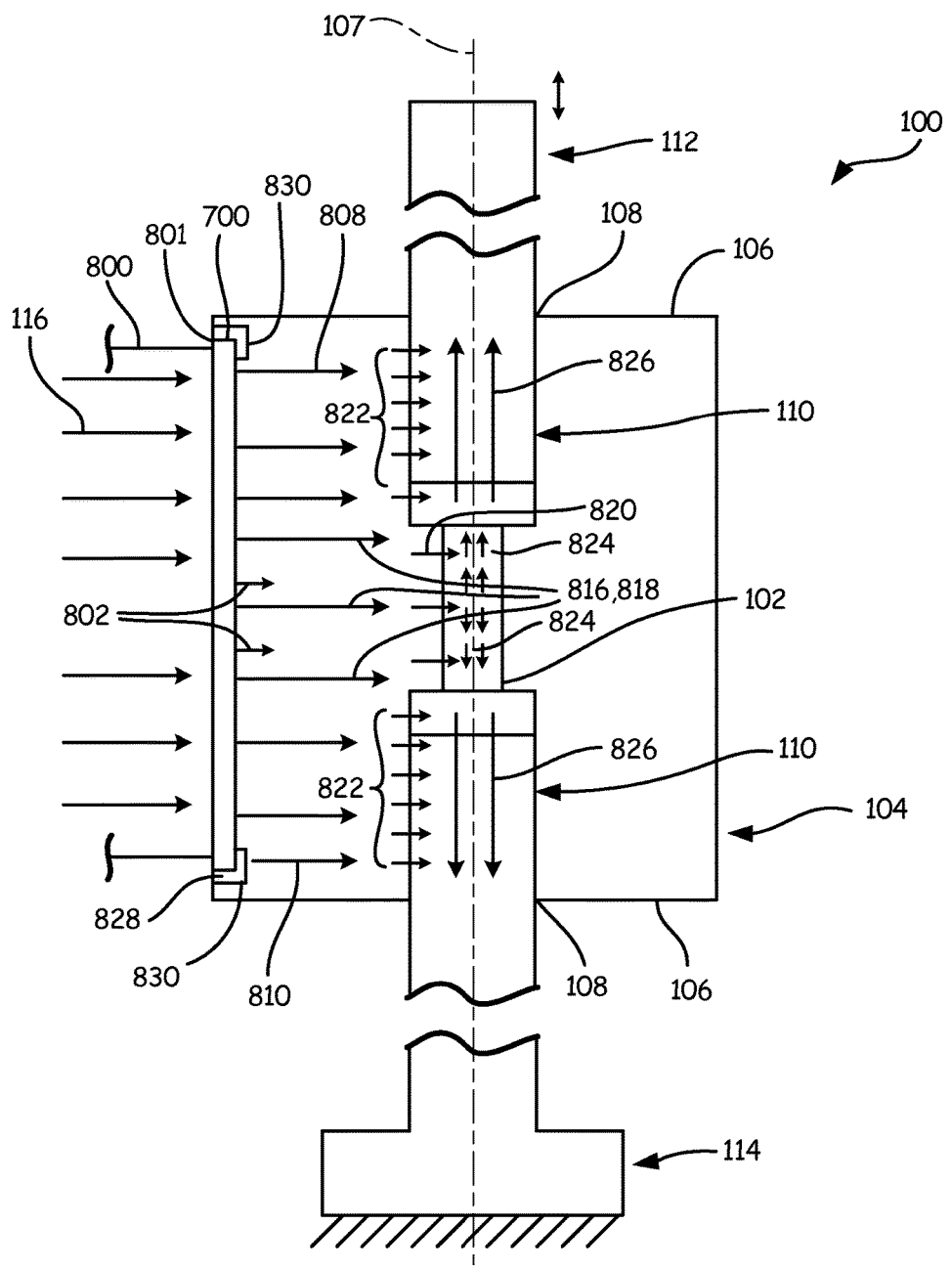
FIG. 8 is a block diagram of a diverter enabled embodiment of the present disclosure.

FIG. 8 schematically shows an embodiment of an environmental chamber 104 employing a diverter 700. Channel or passageway 800 provides forced air flow 116 into environmental chamber 104. In this embodiment, diverter 700 covers the exit opening 801. The relative size of the passageway 800 to the environmental chamber 106 can vary as needed. Air flow 116 is modified by the openings in the diverter 700. Arrows 802 indicate air flow through diverter 700 openings 702. This air flow 802 is substantially directed at specimen 102. Arrows 808 and 810 indicated air flow through diverter 700 openings 708 and 710. Arrows 816, 818 indicate air flow through diverter 700 openings 716 and 718. The air flow represented by arrows 816, 818 is directed past specimen 102, but not directly at specimen 102, and thereby substantially bypasses specimen 102. The lower velocity and volume of air flow indicated impinging upon the specimen 10 and represented by arrows 802 results in lower convective heating of the specimen 102 as indicated at arrows 820, and relatively higher convective heating of extension assemblies 110 as indicated by arrows 822. Conductive heat flow in the specimen 102 is indicated by arrows 824 and conductive heat flow in the extension assemblies 110 is indicated by arrows 826. The air flow pattern in environmental chamber 104 as modified by diverter 700 increases the temperature of the portions of the extension assemblies 110 proximate their engagement with the specimen 102, and makes and/or maintains the portions of the extension assemblies 110 proximate the specimen 102 closer in temperature to that of the specimen 102, reducing conductive heat flow 824 from the specimen 102 to the extension assemblies 110 by reducing the temperature gradient between the specimen 102 and the extension assemblies 110, and then as a result, reducing the temperature gradient within the specimen.

Diverter 700 is connected to opening 801 in one embodiment by a hinge 828, so that diverter 700 may be removed from the air flow path 116. Alternative mountings of diverter 700 to opening 801 include by way of example only and not by way of limitation press fitting, screwing, riveting, or the like, and other mounting structures may be employed without departing from the scope of the disclosure. The mounting structures may be configured to allow easy removal of the diverter 700 such as slots or guides 830 formed in the environmental chamber 106 that engage one or more portions of the perimeter edges of the diverter 700. Structures that allow easy removal allow diverters having different air diverting characteristics to be tried until a diverter that achieves the desired or at least acceptable temperature gradient within the specimen 102, at least in part by reducing the temperature gradient between the specimen and the portions of the assemblies 110 proximate the specimen 102.

Cold temperature applications are the most applicable for DMA testing. The cold temperature case is similar to the hot temperature case described herein, except that air temperature is always colder than the specimen and extension assemblies, and the heat transfer path is reversed, as shown in FIG. 2. For cold testing, the direction of thermal energy is from the outside of the chamber 106, through the extension assemblies 110, into the specimen 102, and then out of the specimen 102 and into the air flow. All benefits of the air flow diverters described herein are the same in the cold temperature case as in the hot temperature case, except that convective and conductive flow paths are reversed.

Figure 9:
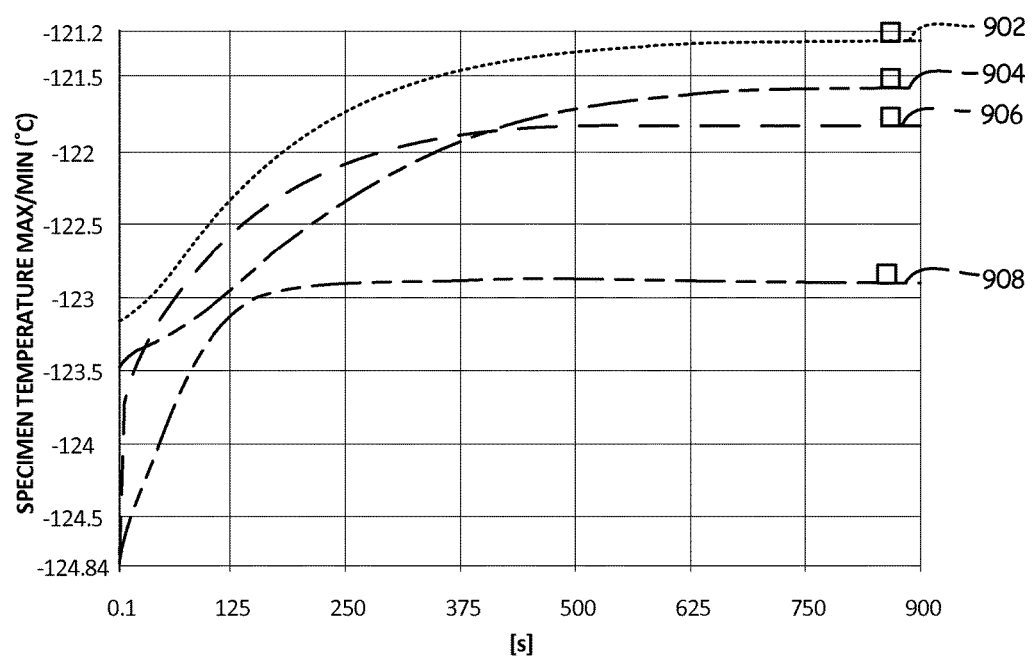
FIG. 9 is a graph of simulated maximum and minimum specimen temperatures according to an embodiment of the present disclosure.

FIG. 9 shows simulated maximum and minimum specimen temperatures for a 2° C. air flow temperature step (from −125 to −123° C.). The maximum temperature curve with a diverter such as diverter 700 is indicated at 902, and the minimum temperature curve with a diverter such as diverter 700 is indicated at 904. Maximum and minimum temperature curves without a diverter are indicated at 906 and 908 respectively. The steady state temperature gradient is much smaller with the diverter. The gradient with the diverter is small during the transient as well.

Figure 11:
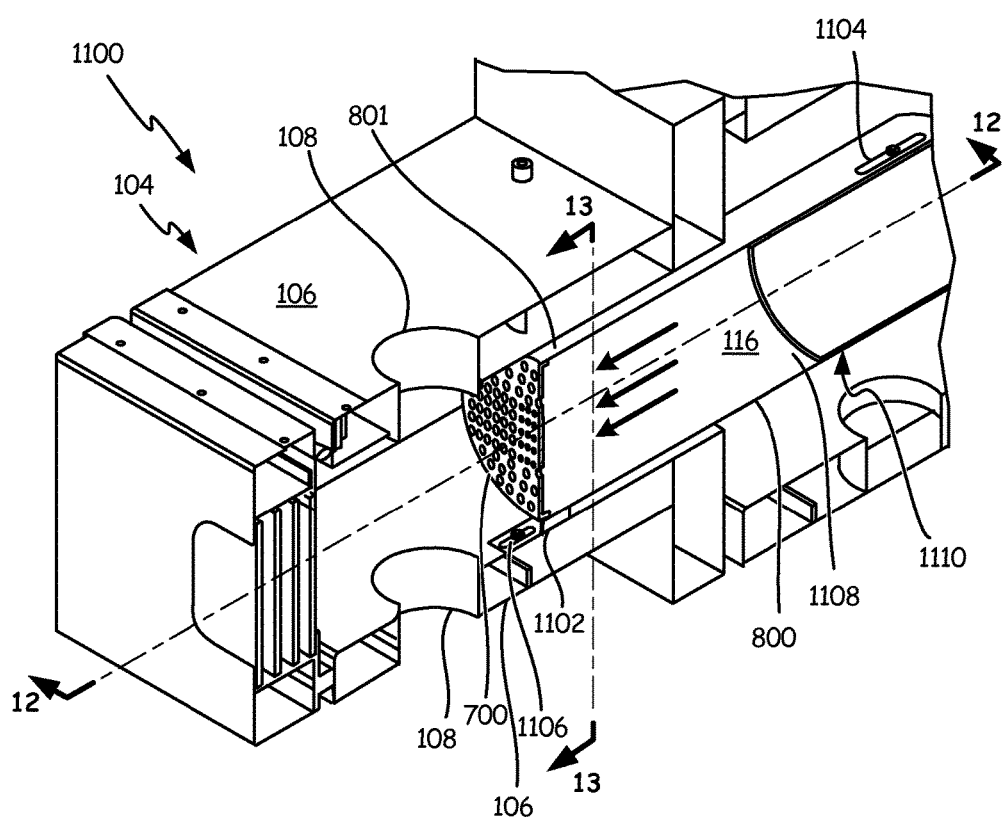
FIG. 11 is a perspective view of a portion of an environmental chamber according to one embodiment of the present disclosure.
Figure 14:
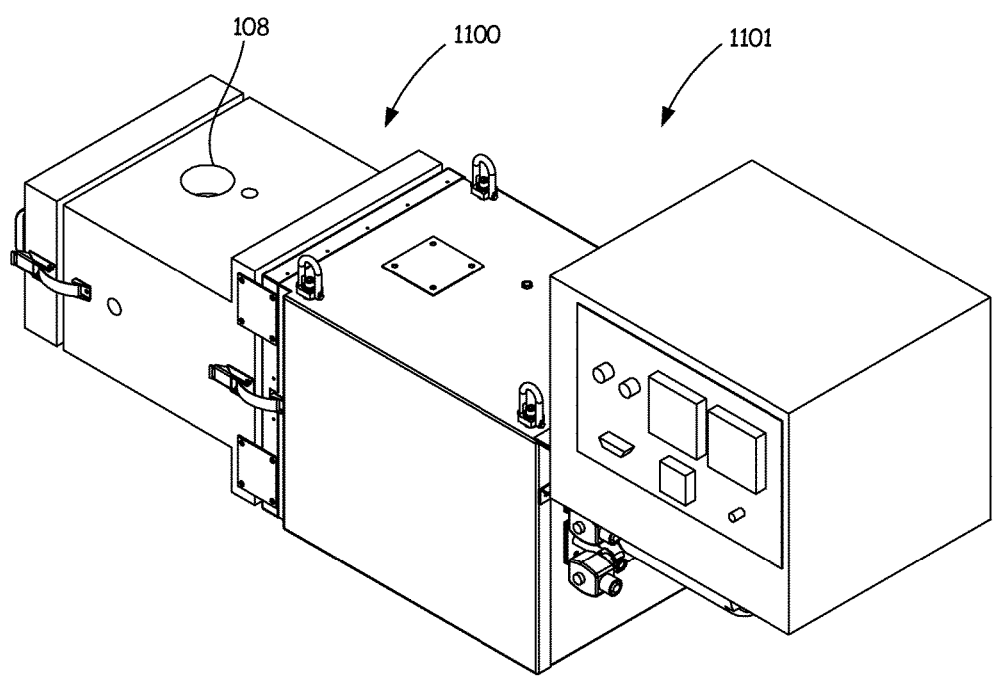
FIG. 14 is a perspective view of an environmental chamber.

FIG. 11 is a perspective view of a portion 1100 of an environmental chamber 1101, an embodiment of a complete assembly of which is illustrated in FIG. 14. The environmental chamber 1101 can be mounted to load frame 100 illustrated in FIG. 10, or adjacent to load frame 100 on a suitable support such that portion 1100 corresponds to environmental chamber 1012 illustrated in FIG. 10, in which case for purposes of the present invention the environmental chamber 1101 is considered part of the load frame 100.

In FIG. 11, conduit 800 is shown with a diverter such as diverter 700 positioned over opening 801. Diverter 700 is connected to conduit 800 at standoff 1102, such as with a screw or other suitable fastening device. Conduit 800 surrounds an end of extension tube 1108 which is in air flow communication with the source of heated/cooled air flow 116. Conduit 800 is in one embodiment connected to extension tube 1108 by a screw or other suitable fastening device extending through slot 1104. In the embodiment illustrated, air passageway 1110 includes conduit 800 and extension tube 1108. In one embodiment, the air passageway 1110 for air directed at the specimen is adjustable in length, which can be helpful in adjusting a position of the diverter 700 relative to a test specimen, not shown. Standoff 1102 also has a slot, 1106, allowing for a movable mounting of conduit 800 such as in a telescoping nature with respect to extension tube 1108. Air return from the interior of chamber 104 is in one embodiment in a space around the conduit 800, through a suitable air return, etc.

Figure 12:
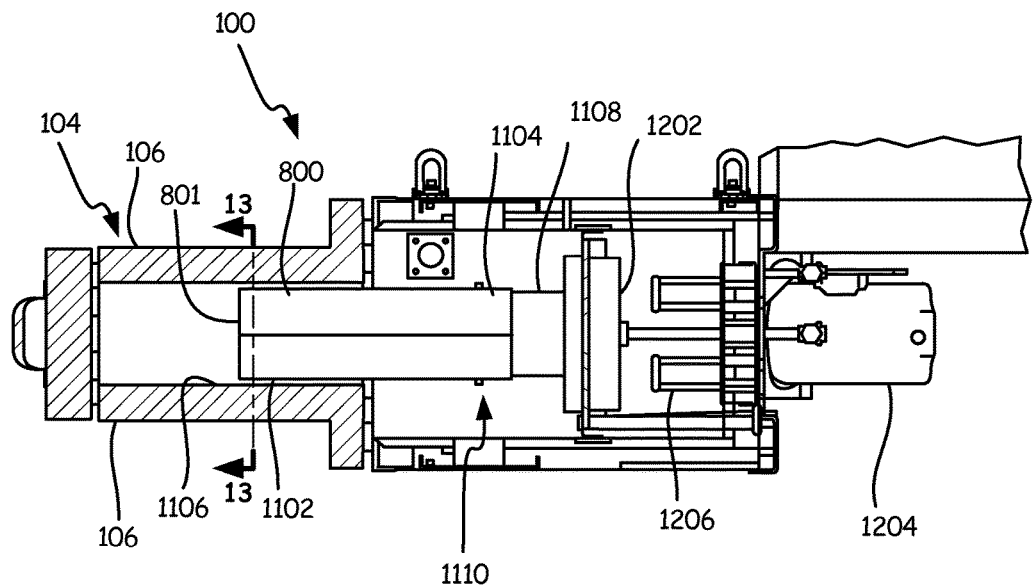
FIG. 12 is an elevation view of FIG. 11 taken along lines 12-12 thereof.

FIG. 12 is an elevation view of FIG. 11 taken along lines 12-12 thereof. In this figure, the diverter 700 is not shown. Air flow 116 is directed into environmental chamber 104 through extension tube 1108 and conduit 800, through opening 801, which in some embodiments may be covered with a diverter such as diverter 700. Air flow, such as air flow 116 described herein, is in one embodiment generated by fan 1202 driven by motor 1204. Heater elements 1206 warm air to be blown by fan 1202 in one embodiment. Cooled air may be introduced in place of heated air, the provision of cooled air known to one of skill in the art, and therefore not described in detail herein.

Figure 13:
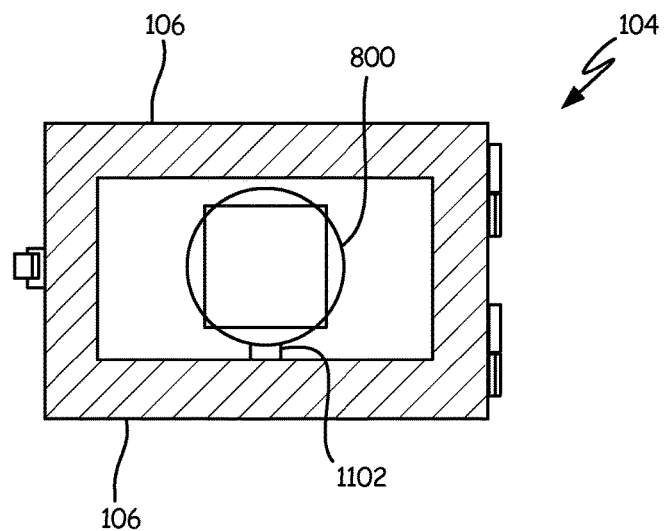
FIG. 13 is an elevation view of FIG. 11 taken along lines 13-13 thereof.

FIG. 13 is an elevation view of FIG. 11 taken along lines 13-13 thereof. In this figure, the diverter 700 is not shown. Conduit 800 is shown mounted to standoff 1102, which also serves in one embodiment as a mount for a diverter such as diverter 700 (not shown).

While the systems described herein are amenable for use with specimens of all types, they are specifically amenable and cost effective for use with specimens that are elastomers or plastics.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. An environmental chamber, comprising:
    an enclosure having opposed walls, each wall having an aperture, the apertures aligned with each other along a reference axis;
    a conduit adjustable in length oriented to provide air directed to the reference axis;
    a forced air source connected to an end of the conduit remote from the reference axis, the forced air source configured to supply forced air to into the enclosure through the conduit in a direction to intersect with the reference axis within the enclosure within the enclosure; and
    a diverter mounted to an opening of the conduit remote from the forced air source,
    the diverter is being located inside the enclosure and is configured to receive the forced air and control air flow past different portions of the reference axis, wherein the conduit is adjustable to adjust a position of the diverter with respect to the reference axis.

2. The environmental chamber of claim 1 wherein the diverter is configured to reduce air flow at a middle portion of the reference axis along its length remote from each of the apertures and increase air flow at first and second end portions of the reference axis along its length, each end portion being located between the middle portion and a respective one of the apertures.

3. The environmental chamber of claim 2 wherein the diverter includes surfaces to deflect air flow toward each of the end portions of the reference axis.

4. The environmental chamber of claim 3 wherein each of the surfaces is oriented oblique to the air flow.

5. The environmental chamber of claim 4 wherein each of the surfaces include apertures extending therethrough.

6. The environmental chamber of claim 2 wherein the diverter includes a first of one or more apertures therethrough to direct air flow to each of the end portions of the reference axis.

7. The environmental chamber of claim 6 wherein the diverter includes a second of one or more apertures therethrough configured to direct air flow to the middle portion of the reference axis.

8. The environmental chamber of claim 7 wherein the second of one or more apertures is disposed between a pair of said first of one or more apertures.

9. The environmental chamber of claim 8 wherein the first of one or more apertures and the second of one or more apertures are disposed on a flat member.

10. A load frame comprising:
a support structure;
an actuator connected to the support structure;
a pair of test specimen supports connected to the support structure and the actuator, each test specimen support configured to hold a portion of a test specimen; and
an environmental chamber, comprising:
an enclosure having opposed walls each wall having an aperture, wherein the apertures being aligned with each other along a reference axis, the pair of test specimen supports configured to hold the test specimen therebetween and on the reference axis;
a conduit adjustable in length oriented to provide air directed to the reference axis;
a forced air source connected to an opening of the conduit remote from the reference axis, the forced air source configured to supply forced air in a direction to intersect with the reference axis within the enclosure at an angle substantially normal to the reference axis; and
a diverter mounted to an end of the conduit remote from the forced air source, the diverter is being located inside the enclosure and is configured to receive the forced air from the forced air source via the conduit and control air flow past different portions of the reference axis, wherein the conduit is adjustable in length to adjust a position of the diverter with respect to the reference axis.

11. The environmental chamber of claim 10 wherein the diverter is configured to reduce air flow at a middle portion of the reference axis along its length remote from each of the apertures and increase air flow at test specimen support portions of the reference axis.

12. The environmental chamber of claim 11 wherein the diverter includes surfaces to deflect air flow toward each of the test specimen support portions of the reference axis.

13. The environmental chamber of claim 10 wherein the diverter includes a first of one or more apertures therethrough to direct air flow to each of first and second end portions of the reference axis.

14. The environmental chamber of claim 13 wherein the diverter includes a second of one or more apertures therethrough configured to direct air flow to a middle portion of the reference axis.

15. The environmental chamber of claim 14 wherein the second of one or more apertures is disposed between a pair of said first of one or more apertures.

16. The environmental chamber of claim 15 wherein the first of one or more apertures and the second of one or more apertures are disposed on a flat member.

17. The environmental chamber of claim 10 wherein the diverter includes a mount configured to adjustably fix the diverter at a selected distance from the reference axis.

* * * * *